(12) United States Patent
Kern et al.

(10) Patent No.: US 7,811,437 B2
(45) Date of Patent: Oct. 12, 2010

(54) CONDUCTIVE MEDIA FOR ELECTROPHORESIS

(75) Inventors: Scott E. Kern, Hunt Valley, MD (US); Jonathan R. Brody, Philadelphia, PA (US)

(73) Assignee: Faster Better Media LLC, Hunt Valley, MD (US)

( * ) Notice: Subject to any disclaimer, the term of this patent is extended or adjusted under 35 U.S.C. 154(b) by 1041 days.

(21) Appl. No.: 11/543,925

(22) Filed: Oct. 6, 2006

(65) Prior Publication Data

US 2007/0131553 A1     Jun. 14, 2007

Related U.S. Application Data

(63) Continuation of application No. 10/980,826, filed on Nov. 4, 2004, now Pat. No. 7,163,610.

(60) Provisional application No. 60/582,427, filed on Jun. 25, 2004, provisional application No. 60/549,984, filed on Mar. 5, 2004, provisional application No. 60/542,876, filed on Feb. 10, 2004, provisional application No. 60/520,645, filed on Nov. 18, 2003.

(51) Int. Cl.
*G01N 27/453* (2006.01)

(52) U.S. Cl. .................. 204/606; 204/605; 204/469; 204/470

(58) Field of Classification Search ......... 204/465–468, 204/455, 456, 605, 606, 616–618
See application file for complete search history.

(56) References Cited

U.S. PATENT DOCUMENTS 4,908,112 A    3/1990   Pace
4,936,963 A    6/1990   Mandecki et al.
4,948,480 A    8/1990   Christy et al.
5,041,203 A    8/1991   Serwer
6,942,773 B1*  9/2005   Olivares et al. ............. 204/452
7,163,610 B2*  1/2007   Kern et al. .................. 204/468

OTHER PUBLICATIONS

Buffer composition list downloaded from http://wheat.pw.usda.gov/~lazo/methods/lazo/buffer.html on Mar. 28, 2010.*

TBE Buffer (10X) description on National Diagnostics web page downloaded from http://nationaldiagnostics.com/product_info.php/products_id/90 on Mar. 28, 2010.*

"Agarose Gel Electrophoresis of DNA" article downloaded from Colorado State edu website http://www.vivo.colostate.edu/hbooks/genetics/biotech/gels/agardna.html downloaded on Mar. 28, 2010, last updated on Jan. 15, 2000.*

Coleman et al., "Electrodialysis of sugar borates", *The Proceedings of the Iowa Academy of Science* 49 (1942) 257-261.

(Continued)

*Primary Examiner*—Alex Noguerola
(74) *Attorney, Agent, or Firm*—Arnold & Porter LLP

(57) ABSTRACT

A series of low molarity conductive media based on non-buffering univalent cations, such as sodium chloride-sodium acetate (SCA), sodium boric acid (SB), lithium boric acid, and lithium acetate mitigate the "runaway" positive feedback heating loop produced by conventional media containing biological amine buffers and permit improved DNA electrophoresis under the conditions of low salt concentration. These media serve well in ultra-fast DNA electrophoresis and in high-resolution separations of RNA and DNA fragments.

19 Claims, 8 Drawing Sheets

OTHER PUBLICATIONS

Consden et al., Ionophoresis of sugars on paper and some applications to the analysis of protein polysaccharide complexes, *Nature* 1952; 169:783-785.

Matsubara et al., "Electrophoretic separation of single-stranded deoxyibonucleic acid from double-stranded deoxyribonucleic acid", *Biochim Biophys Acta* 1962; 55:389-392.

Bachvaroff et al., "Separation of microsomal RNA into five bands during agar electrophoresis", *Science* 1964; 143-1177-1179.

Peacock et al., "Serum Protein Electrophoresis in Acrylamide Gel: Patterns from Normal Human Subjects", *Science* 1965; 147:1451-1453.

Richards et al., "Disc electrophoresis of ribonucleic acid in polyacrylamide gels", *Anal Biochem* 1965; 12:452-471.

Thorne, "Electrophoretic separation of polyoma virus DNA from host cell DNA", *Virology*, 1966; 29:234-9.

Peacock et al., "Resolution of Multiple Ribonucleic Acid Species by Polyacrylamide Gel Electrophoresis",. *Biochem* 1967; 6:1818.

Loening, "The Franctionation of High-Molecular-Weight Ribonucleic Acid by Polyacrylamide-Gel Electrophoresis", *Biochem J* 102 (1967) 251-257.

Takahashi et al., "Estimation of relative molecular length of DNA by electrophoresis in agarose gel", *Biochim Biophys Acta* (1969) 174:183-7.

Danna et al., "Specific cleavage of simian virus 40 DNA by restriction endonuclease of Hemophilus Influenzae", *Proc Natl Acad Sci USA* 1971; 68(12)2913-7.

Aaij et al., "The gel electrophoresis of DNA", *Biochim Biophys Acta* 1972; 269(2):192-200.

Hayward et al., "The chromosome of bacteriophage T5. I. Analysis of the single-stranded DNA fragments by agarose gel electrophoresis", *J Mol Biol* 1972; 63(3):383-95.

Lehrach et al., "RNA molecular weight determinations by gel electrophoresis under denaturing conditions, a critical reexamination", *Biochemistry* 1977; 16:4743-51.

Goldberg, "Isolation and partial characterization of the Drosophila alcohol *dehydrogenase* gene", *Proc Natl Acad Sci USA* 1980; 77:5794-5798.

Kukita et al., "SSCP analysis of long DNA fragments in low pH gel", *Hum Mutat* 1997; 10:400-7.

Liu et al., "pK-matched running buffers for gel electrophoresis", *Anal Biochem* 1999; 270:112-22.

Heller et al., "Principles of DNA separation with capillary electrophoresis", *Electrophoresis* 2001; 22:629-643.

Brody et al., "Sodium boric acid: a Tris-free, cooler conductive medium for DNA electrophoresis", *Biotechniques* 2004; 36:214-6.

Brody et al., "Ultrafast high-resolution agarose electrophoresis of DNA and RNA using low-molarity conductive media", *Bio Techniques* 2004; 37:598-602.

Brody et al., "History and principles of conductive media for standard DNA electrophoresis", *Anal Biochem* 2004; 333:1-13.

Emanuela Handman: Faculty of 1000, Mar. 8, 2004 http://www.f1000biology.com/article/14989083/evaluation.

Ugaz et al., Phil Trans R Soc Lond 2004; 362:1105-1129.

McMaster et al., "Analysis of single- and double-stranded nucleic acids on polyacrylamide and agarose gels by using glyoxal and acridine orange", *Biochemistry* 74(11) 4835-4838 (1977).

Peacock et al., "Molecular Weight Estimation and Separation of Ribonucleic Acid by Electrophoresis in Agarose-Acrylamide Composite Gels", *Biochemistry* 7(2) 668-674 (1968).

Germond et al., "Folding of the DNA Double Helix in Chromatin-like Structures from Simian Virus 40", *Proc Natl Acad Sci USA* 72(5) 1843-1847(1975).

Chamberlain, "Isozyme variation in Calliandra Calothyrsus (Leguminosae): Its implications for species delimitation and conservation", *Am. J. Botany* 85(1) 37-47 (1998).

Tadesse et al., "Isozymes variability of grasspea (*Lathyrus sativus* L.) in Ethiopia", *Lathyrus Lathyrism Newsletter* 2:43-46 (2001).

Webpage www.ceandcec.com/generic.htm from Jun. 24, 2003, "Generic CE method operating conditions", 22 pages. Available from www.archive.org.

Hrkal, "Gel Type Techniques", Chapter 6 of "Electrophoresis: A survey of Techniques and Applications, Part A: Techniques" Z. Deyl, ed., New York: Elsevier (1979) p. 113-131.

Zak et al., "Rapid Electrophoresis of RNA nucleotides in a dilute agar gel paper medium", *J. Chromatogr* 13, 255-258 (1964).

Crestfield et al., "Resolution of Ribonucleotides by Zone Electrophoresis", *Anal. Chem.* 27(3) 424-425 (1955).

Website www.nexusresearchgroup.com/fun_science/electrophoresis.htm from Aug. 30, 2002, "Nexus Research Group—FUN Science and home experiments . . . ", 3 pages. Available from www.archive.org.

Website www.accessexcellence.org/AE/AEPC/DNA/detection.htm from Mar. 10, 2000, "Detection of Alu by PCR", 3 pages. Available from www.archive.org.

Constans, "Building a Better Buffer", *The Scientist*, 18(5): 39 (Mar. 15, 2004).

International Search Report for PCT/US04/37042 dated Sep. 19, 2005.

Weiner et al., "Rapid Electrophoresis of Nucleic Acid Basis in Agar Gel on Teflon-Glass Paper", *Clin. Chim. Acta.* 9:407-409 (1964).

Isaaq et al., "The Effect of Electric Field Strength, Buffer Type and Concentration on Separation Parameters in Capillary Zone Electrophoresis", *Chromatographia*, 32, 155-161 (1991).

Oana et al., "High-Speed Separation of Linear and Supercolled DNA by Capillary Electrophoresis. Buffer, Entangling Polymer, and Electric Field Effects", *Anal. Chem.* 70, 574-579 (1998).

\* cited by examiner

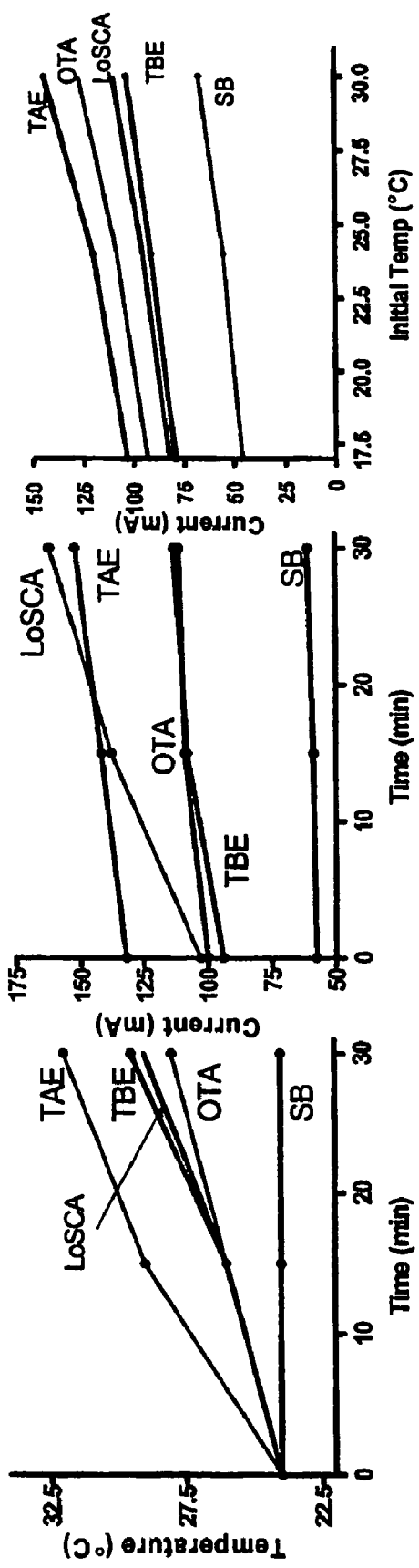
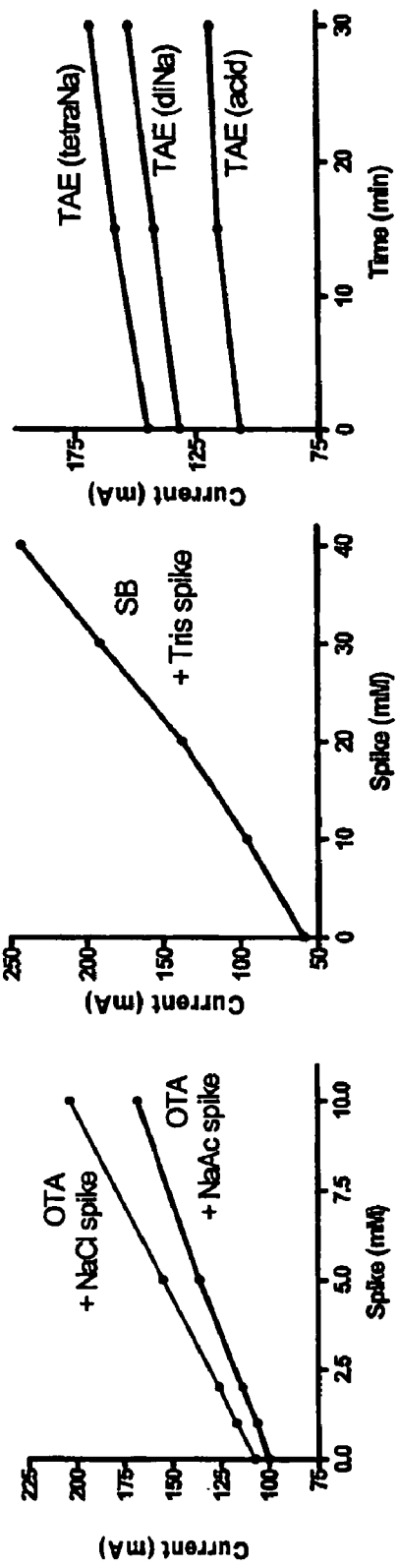
FIG. 1A, FIG. 1B, FIG. 1C, FIG. 1D, FIG. 1E, FIG. 1F

FIG. 6A

A  1 mM conductive media-25V/cm

| | Cs | Rb | Li | Ea | K | TAE | TBE |
|---|---|---|---|---|---|---|---|
| Initial current | 24 | 21 | 15 | 15 | 16 | 228 | 178 |
| Final current | 22 | 19 | 15 | 14 | 15 | 365 | 270 |
| ΔT | 0 | 0 | 0 | 0 | 0 | 20 | 17 |

◄ 650 bp

B  1 mM conductive media-100V/cm

| | Cs | Rb | Li | Ea | K | Na |
|---|---|---|---|---|---|---|
| Initial current | 85 | 90 | 60 | 55 | 68 | 70 |
| Final current | 80 | 88 | 55 | 55 | 60 | 68 |
| ΔT | 3 | 3 | 2 | 1 | 2 | 2 |

FIG. 7A
A  5mM Li acetate-30V/cm
Initial current (mA) 74
Final current 123
$\Delta T$ (°C) 12
◀ 12,000 bp
◀ 5,000 bp
◀ 2,000 bp
B  Low-molarity media
RNA agarose electrophoresis
1    2
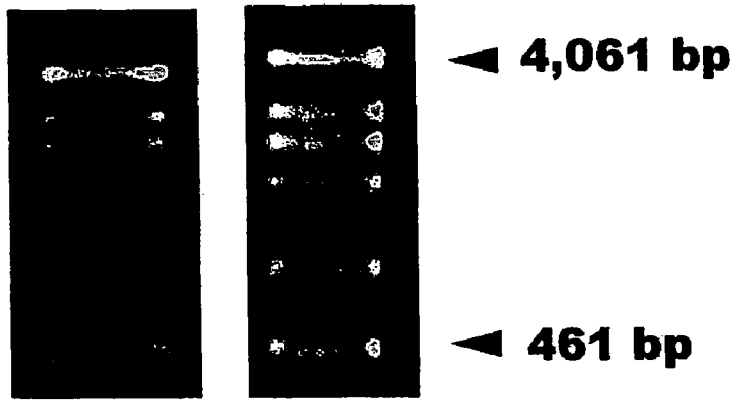
◀ 4,061 bp
◀ 461 bp
FIG. 7B

CONDUCTIVE MEDIA FOR ELECTROPHORESIS

CROSS-REFERENCE TO RELATED APPLICATIONS

This application is a continuation of U.S. application Ser. No. 10/980,826, filed Nov. 4, 2004, now U.S. Pat. No. 7,163,610 which claims the benefit of U.S. Provisional Application No. 60/582,427, filed Jun. 25, 2004, U.S. Provisional Application No. 60/549,984, filed Mar. 5, 2004, U.S. Provisional Application No. 60/542,876, filed Feb. 10, 2004, and U.S. Provisional Application No. 60/520,645, filed Nov. 18, 2003; each of which is incorporated by reference in its entirety.

This invention was funded using U.S. government finds under NIH award CA62924. The U.S. government therefore retains certain rights in the invention.

FIELD OF THE INVENTION

The invention relates to the field of electrophoresis. In particular it relates to electrophoresis of biological macromolecules.

BACKGROUND OF THE INVENTION

It has been nearly three decades since the invention of DNA electrophoresis (1-5), and molecular biology laboratories still rely upon the separation of DNA, from plasmid DNA to PCR products, by use of denaturing or non-denaturing gel electrophoresis (1). Current conductive media for DNA electrophoresis are largely restricted to legacy Tris-acetic acid-disodium EDTA (TAE) and Tris-boric acid-disodium EDTA (TBE) at substantial ionic strengths, leading to higher cost and excessive heat generation and limiting the voltage and speed of electrophoretic runs (for description of buffers see Table 1). Investigators have compared and analyzed TAE and TBE buffers in DNA electrophoresis; however, to our knowledge no one has substantially investigated the simplification and substitution of components of these buffers to achieve a more efficient conductive medium for DNA electrophoresis (6). Conductive media for DNA electrophoresis derived essentially unchanged from RNA gel methodology, which in turn was adapted from a subset of buffers used for protein electrophoresis in the early 1960's (4, 7). The most common DNA electrophoretic media have contained Tris, an organic amine, as their primary cation; the first edition of *Molecular Cloning* (1982) contained a table of the three commonly used buffers for agarose gel electrophoresis: Tris-acetic acid-disodium EDTA, Tris-phosphate-disodium EDTA, and Tris-boric acid-disodium EDTA (1, 8). Presently, Tris-based buffers (TBBs) remain predominant in nearly all molecular biologic research and clinical laboratories (9). TBBs usually contain between 40 to 80 mM Tris (predominantly ionized), corresponding anion concentrations, as well as trace amounts of different forms of EDTA (1-2 mM), which could inhibit nucleases and certain enzymatic reactions. These high concentrations were historically supported by a preference to avoid ions of high mobility (7), to overcome detrimental effects on resolution of DNA-borate complexation by use of higher borate concentrations (6, 10), and to avoid the problems of dilute TAE media (10, 11). Tris is at times used with or replaced by other organic amines that buffer pH in the biological range.

It is well established that heat generation is a primary source of problems in gel electrophoresis, is responsible for sample diffusion, convection, denaturation, and poor gel integrity, and limits the ability to run gels at a high voltage (12). Ohm's law and the power law interrelate voltage (V), current (I), and power (P)(13, 14). Power consumed in the electrophoresis system manifests as heat; heat generation=P=VI. These interrelated variables are affected by ionic conductance due to choice of salts and ionized components in proportion to their particular concentrations in the media used in electrophoresis. The concentration of salts also determines the stability of the double-helical structure of DNA—a melted, single-stranded DNA (ssDNA) structure being desirable for certain DNA electrophoretic techniques.

There is a need in the art for improved conductive media for carrying out electrophoresis of nucleic acids.

BRIEF SUMMARY OF THE INVENTION

In a first embodiment of the invention a method is provided for electrophoretically separating polynucleotides of different sizes. A conductive medium is used to carry a current from one electrode to another. The conductive medium comprises at least 0.5 mM anions in addition to any chloride anions which are optionally present. The conductive medium comprises less than 50 mM of total ions and does not contain an organic amine biological buffer. Alternatively, the conductive medium comprises one to 30 mM of total ions, inclusive, and contains an organic amine biological buffer at a concentration of less than 10 mM. Polynucleotides are spatially separated between the electrodes.

In a second embodiment of the invention a gel is provided for separating polynucleotides according to length of the molecules. The gel comprises a matrix substance and a conductive medium. The conductive medium comprises at least 0.5 mM anions in addition to any chloride anions which are optionally present. The conductive medium comprises less than 50 mM of total ions and does not contain an organic amine biological buffer. Alternatively, the conductive medium comprises one to 30 mM of total ions, inclusive, and contains an organic amine biological buffer at a concentration of less than 10 mM. Polynucleotides are spatially separated between the electrodes.

In a third embodiment of the invention a solution is provided for making a gel for separating polynucleotides according to length of the molecules. The solution comprises: a conductive medium and a polymerizing agent for polymerizing a gel matrix substance. The conductive medium comprises at least 0.5 mM anions in addition to any chloride anions which are optionally present. The conductive medium comprises less than 50 mM of total ions and does not contain an organic amine biological buffer. Alternatively, the conductive medium comprises one to 30 mM of total ions, inclusive, and contains an organic amine biological buffer at a concentration of less than 10 mM. Polynucleotides are spatially separated between the electrodes.

In a fourth embodiment of the invention an electrophoretic apparatus is provided. The apparatus comprises a gel, two or more reservoirs contiguous with the gel, and an anode and a cathode in contact with the reservoirs. The reservoirs and the gel comprise a conductive medium which comprises at least 0.5 mM anions in addition to any chloride anions which are optionally present, and less than 50 mM of total ions, wherein the conductive medium does not contain an organic amine biological buffer. Alternatively, the conductive medium comprises one to 30 mM of total ions, inclusive, and contains an organic amine biological buffer at a concentration of less than 10 mM.

In a fifth embodiment of the invention a method is provided for forming a gel. A gel matrix substance and a conductive medium are mixed to form a pre-gel mixture. The conductive medium comprises at least 0.5 mM anions in addition to any chloride anions which are optionally present, and less than 50 mM of total ions; the conductive medium does not contain an organic amine biological buffer. Alternatively, the conductive medium comprises one to 30 mM of total ions, inclusive, and contains an organic amine biological buffer at a concentration of less than 10 mM. The pre-gel mixture is incubated under conditions in which a gel forms.

In a sixth embodiment of the invention an electrophoretic apparatus is provided. The apparatus comprises a viscous liquid in a container, and an anode and a cathode in contact with the viscous liquid. The viscous liquid comprises a conductive medium which comprises at least 0.5 mM anions in addition to any chloride anions which are optionally present. In addition, the conductive medium comprises less than 50 mM of total ions and does not contain an organic amine biological buffer. Alternatively, the conductive medium comprises one to 30 mM of total ions, inclusive, and contains an organic amine biological buffer at a concentration of less than 10 mM.

In a seventh embodiment of the invention a kit for forming a gel is provided. The kit comprises a solid mixture for dissolving in water to form a conductive medium, a gel matrix substance, and instructions. The conductive medium comprises at least 0.5 mM anions in addition to any chloride anions which are optionally present, and less than 50 mM of total ions. The conductive medium does not contain an organic amine biological buffer. Alternatively, the conductive medium comprises one to 30 mM of total ions, inclusive, and contains an organic amine biological buffer at a concentration of less than 10 mM. The instructions describe how to form a gel by dissolving the solid mixture in sufficient water to form the conductive medium.

In an eighth embodiment of the invention a kit is provided for forming a gel. The kit comprises a concentrated liquid for diluting in water to form a conductive medium, a gel matrix substance, and instructions. The conductive medium comprises at least 0.5 mM anions in addition to any chloride anions which are optionally present, and less than 50 mM of total ions. The conductive medium does not contain an organic amine biological buffer. Alternatively, the conductive medium comprises one to 30 mM of total ions, inclusive, and contains an organic amine biological buffer at a concentration of less than 10 mM. The instructions describe how to form a gel by diluting the concentrated liquid in sufficient water to form the conductive medium.

BRIEF DESCRIPTION OF THE DRAWINGS

FIGS. 1A-1F show analysis of the effects of conductive media on current and temperature during electrophoresis. (FIG. 1A) Heat generation by conductive media over time during electrophoresis at constant voltage (150V). (FIG. 1B) Conductance of media over time at constant voltage (150V). (FIG. 1C) The effect of external heating of conductive media on conductance. Solutions were heated or cooled to 17° C., 24° C., and 30° C. and the current immediately measured. (FIG. 1D) The effect of trace NaCl and NaAc, in conventional media. Salts were spiked into a simplified Tris-based solution at 150V and current immediately measured. (FIG. 1E) The effect of Tris on conductance. Tris was spiked into SB, at amounts up that of conventional media, at 150V and current immediately measured. (FIG. 1F) The concentrations of different forms of EDTA used in electrophoretic media were compared at constant voltage (150V) during electrophoresis. Lines connect the measured data points (filled circles).

(FIG. 3A) The graph plots the empirical nature of the performance of SCA media FIG. 3B) LoSCA (10 mM NaAc and 2.5 mM NaCl) run at standard electrophoretic conditions (8 V/cm, >1 hr). (C) HiSCA (11 mM NaCl and 1.5 mM NaAc) run at standard electrophoretic conditions (8V/cm, >1 hr). Ladder and an unpurified PCR product in reaction buffer were applied using the indicated loading solutions (see Materials and Methods).

(FIG. 4A) An SB gel run at standard conditions (8V/cm). A ladder and unpurified PCR product in reaction buffer were applied using different loading solutions, as indicated. SB gels had flexibility in loading conditions. (FIG. 4B) An SB gel run fast (30V/cm, 13 min). All lanes used SB-based loading solution. The ladder is run as three replicates. (FIG. 4C) Gel-extracted restriction digested plasmid DNA from an SB gel is analyzed on an SB gel. Two separate DNA inserts were run.

(FIG. 5A) Electrolyte exhaustion. Conductive media were tested for exhaustion by plotting the current at constant voltage (200V). (FIG. 5B) pH changes of conductive media analyzed in the cathodic electrode during electrophoresis (10V/cm, 1 hr). (FIG. 5C) pH changes of conductive media analyzed in the anodic electrode during electrophoresis (10V/cm, 1 hr).

FIG. 6A-6C. Conductive media at one-mM cation concentration rapidly separate low molecular weight DNA in agarose. All cations were paired with boric acid. Cations are represented by their elemental symbol, except for ethanolamine (Ea). $\Delta T$ is given in ° C. and current in milliamperes. (FIG. 6A) 100 bp resolution. 250V were applied for 25 min. A DNA marker (Invitrogen) had fragments at 100, 200, 300, 400, 500, and 650 bp. (FIG. 6B) 20 bp resolution. A very high voltage (1000V) was applied for 5.5 minutes (as compared to the conventional 90 min). A DNA marker (GenSura) had fragments at 20, 40, 60, 80, and 100 bp. The pH of the conductive media at 1 mM was approximately 8.2. (FIG. 6C) 1 bp resolution. ssDNA oligomers were run on 3% agarose gels at 29V/cm for 25 min, with an initial gel temperature of 37° C. The samples were denatured by heat (70° C. for five min.) prior to loading on the gel. Each lane was loaded with a different size oligomer mixed with a 35-oligomer.

FIG. 7A to 7B. Fast separation of high molecular weight DNA and RNA using low-molarity conductive media (FIG. 7A) 1000 bp resolution. A high voltage (300V) was applied for less than 30 min. The illustrated DNA marker (Invitrogen) comprises 1.6 kb, and 2 Kb to 12 Kb in 1 Kb increments. The pH of 5 mM lithium acetate was approximately 6.5. (FIG. 7B) Low-molarity media used to separate RNA. 1.0% agarose-formaldehyde gels were run at 40V/cm for 10 minutes. An RNA marker (New England Biolabs) had fragment sizes of 461 to 4,061 bases as indicated. Lane 1 represents a 5 mM lithium acetate agarose gel and lane 2 represents a 5 mM sodium boric acid gel (pH=6). The initial current for the sodium boric acid medium was 44 mA and the final current was 47 mA. The $\Delta T$ was 8° C. The initial current for the lithium acetate medium was 56 mA and the final current was 80 mA. The $\Delta T$ was 9° C. In contrast, a 1×MOPS (20 mM MOPS, 7 mM sodium, 1 mM EDTA)(not shown) at the same voltage had an initial current of 93 mA and a final current of 119 mA. The $\Delta T$ was 15° C.

DETAILED DESCRIPTION OF THE INVENTION

Figure 6C:
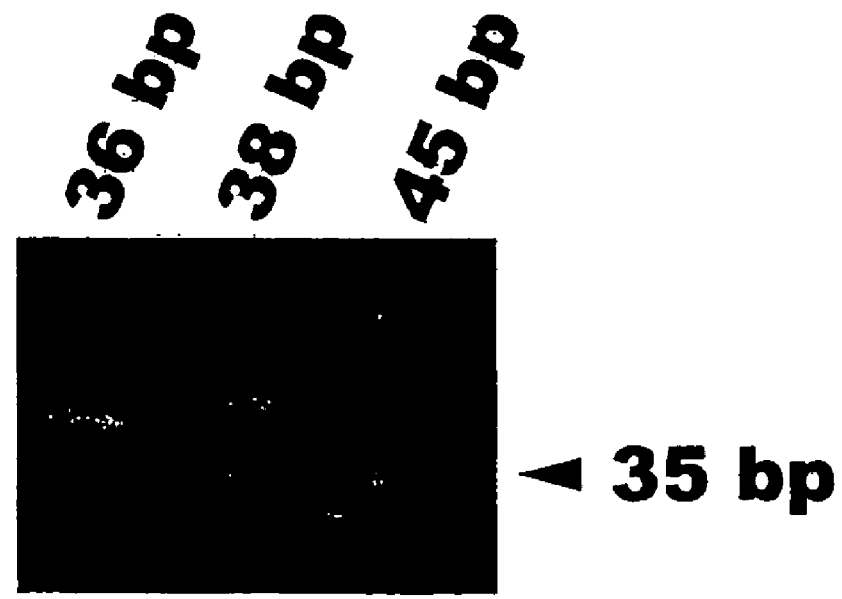

It is a discovery of the present inventors that high-resolution electrophoretic separation of biological macromolecules, such as polynucleotides, can be advantageously accomplished using low-salt conditions. Moreover, pH buffering capacity is not of critical importance. Such conditions lead to lower heat generation, allowing rapid electrophoresis at higher voltage than possible at higher ionic strength, and permit the separation of short DNA fragments and ssDNA at high resolution under more convenient conditions. For example, very low ionic conditions for the electrophoresis of ssDNA in a gel enable electrophoresis to readily occur while reducing or eliminating the need for chemical additives to the gel, such as urea and formamide, that serve to 'melt' or maintain DNA in a melted (single-stranded) conformation (FIG. 6C).

Electrophoresis is the process by which electrically charged biological polymers can be moved through a solvent in an electric field. The solvent can be a liquid or a gel. To prevent diffusion, it may be desirable for the liquid to have a high viscosity. A gel or viscous medium for conducting electrophoretic separations of nucleic acids can be made by any matrix substance known in the art. These include polyacrylamide, agarose, starch, and combinations of such matrix substances. The matrix substance may be cross-linked to increase mechanical strength. The matrix substance may have a chromatographic effect by adsorbing or sieving, but such is not necessary.

Buffers may be used in the practice of the invention, but they are not required. Organic amine biological buffers, such as HEPES, Tris, TAPS, bicine, ACES, MES, CAPSO, and MOPS are commonly used in biological applications. These buffers are used for buffering solutions in the physiological range of 6.0 to 8.5. Such buffers are not required in the practice of the invention. If used, the organic amine biological buffer are present at a concentration of less than 10 mM, less than 5 mM, less than 2.5 mM, or less than 1 mM.

The conductive media of the present invention can be used in any electrophoretic configuration known in the art. The electrophoresis can be carried out in liquid, semi-solid, or gel, for example. The shape of the gel can be a slab, a thin layer, a column, a capillary, etc. Viscous solutions and gels form a continuum physically and in scientific parlance; indeed, viscous solutions of polymers capable of a sieving property, such as are solutions formed by linear polyacrylamide, are often referred to as "gels."

Kits for forming gels typically are packaged in a container, which is divided or undivided, and which may contain additional containers within. The components for forming the conductive medium may be supplied in separate containers or pre-mixed. The components may be in a liquid or solid form. If the components are in a liquid form, the kit will typically contain instructions for diluting the liquid. If the components are in a solid form, the kit will typically contain instructions for dissolving the components. The instructions may be verbal or pictorial. They may be printed on paper or embodied on an electronic medium, such as a compact disk. The instructions may be embodied in the kit as a website address. The kit may optionally comprise other items, such as a gel matrix substance, e.g. agarose or polyacrylamide, cross-linking agents, polymerizing agents, containers in which to form a gel, molecular weight standards, and dyes.

While some ions are necessary for electrophoresis to occur, the inventors have found that a high concentration of ions is not necessary. At a minimum, the conductive medium of the invention should have at least 0.5 mM of anions which are not chloride ions. Chloride ions, however, need not be present. The concentration of anions may be at least 0.5 mM, at least 5 mM, at least 10 mM, at least 15 mM, or at least 20 mM. For particular circumstances, the concentration of total ions is desirably less than 40 mM, less than 30 mM, less than 25 mM, less than 20 mM, less than 15 mM, less than 10 mM, or less than 5 mM. The pH of the conductive medium is preferably greater than 5, greater than 6, or greater than 7, but less than 11, less than 10, or less than 9.

Any cations and anions can be used within the concentration and pH parameters set forth above. Anions which can be used advantageously according to the invention include chloride, carbonate, acetate, borate, phosphate, formate, and salicylate. Cations which can be used include without limitation sodium, potassium, ethanolamine, ammonium, lithium, rubidium, and cesium. Mixtures of cations and mixtures of anions can be used. Thus the concentration of any individual ion may fall below a stated lower limit, so long as the total concentration falls within the stated ranges.

A capillary enclosure in its most common form is a capillary tube, less than 2 mm in internal diameter, made of fused silica that guides a single electrophoretic path of the polynucleotides being separated, appropriate for loading a single sample in a limited time period. An essentially equivalent capillary enclosure that guides a single path of electrophoretic separation can be made of other materials or drilled into a solid material, such as employed in microfabricated devices. A capillary enclosure is generally distinguished from the other major electrophoretic design, that of slab gel electrophoresis, by an individual capillary unit having a small cross-sectional area (i.e., less than about 5 mm) and by its containment of only one electrophoretic path, whereas individual slab gels usually comprise many paths in parallel, permitting loading of multiple samples and simultaneously separating them spatially within the same gel.

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

EXAMPLES

Example 1

Materials and Methods

Studies of conductance, temperature, and voltage used a horizontal gel rig (MGU-500, CBS, Del Mar, Calif.) and a power source that provided current readings at set voltages (FB 570, Fisher Biotech, Pittsburgh, Pa.). All media were analyzed at the same volume (650 ml) in the reservoir. 1.2% agarose (Type I: low EEO Agarose, Sigma, St. Louis, Mo.) gels containing 0.2 microgram/ml ethidium bromide (EtBr) (Fischer Scientific, Fair Lawn, N.J.) were used except as noted. Tris-EDTA (TE) solution was purchased from Invitrogen, Carlsbad, Calif. (1×TE: 10 mM Tris-HCl, 1 mM EDTA).

A DNA marker (1 Kb plus, Invitrogen) was used as a test sample. Sodium chloride (NaCl), sodium hydroxide (NaOH), sodium acetate (NaAc), potassium hydroxide (KOH), and potassium chloride (KCl) were bought from J. T. Baker (Phillipsburg, N.J.). Tris and all forms of EDTA were bought from USB (Cleveland, Ohio). A 1× loading solution matched to each conductive media was used as indicated in the figures. All loading solutions contained 0.5% N-lauroyl sarcosine sodium salt (ICN Biochemicals, Cleveland, Ohio), 0.05% orange G (Sigma), and 20% glycerol (USB) in a given conductive medium. Gel extraction was performed with the Qiagen Gel Extraction Kit (Qiagen, Valencia, Calif.). Other chemicals were bought from Sigma Gel resolution studies were performed in MGU-500 and MGU-502T units (CBS). Gel resolution studies were validated and polyacrylamide gels were used in larger vertical gel rigs (SE 600, Hoefer Scientific Instruments, San Francisco, Calif.).

For denaturing gels, a 24:1 polyacrylamide (Grade A Accurate Chemical and Scientific Co., Westbury, N.Y.) and bis-acrylamide (USB) solution was used to make a final concentration of 20% acrylamide (0.2% EtBr), 6 M urea in the Hoefer rig using a 1 mm spacer. Ammonium persulfate (J. T. Baker) and TEMED (USB) were used to polymerize. Two oligos (21 and 25-mers) of complimentary sequence were analyzed denatured and annealed (Integrated DNA Technologies, Coralville, Iowa).

Example 2

Conventional Media and Heat

A thorough analysis of the critical properties of widely used buffered media for DNA electrophoresis was performed. At constant voltage, we found that a positive feedback loop existed between the temperature of the buffer and the current for all TBBs (FIG. 1a-c). At constant voltage, TAE and TBE experienced increased temperature and current over time (FIG. 1a,b). To verify that temperature and current were directly interrelated (a known feature of electrolyte solutions) we manipulated the temperature of the buffered media (13, 14). For all TBBs, external heating of the conductive media resulted in a direct increase in current (FIG. 1c). Superfluous sodium ions as well as the high amount of Tris ions (Table 1) in these buffers were found to be responsible for producing unnecessary current and limited the ability to run gels at a high voltage; the addition of millimolar amounts of NaCl or NaAc to a simple Tris-acetic acid (30 mM Tris) medium increased current almost two-fold under constant voltage (FIG. 1d). Since a reduced current would directly mitigate heat generation, the results supported the notion that low ionic strength buffers would be optimal for DNA electrophoresis and that superfluous ions should be avoided.

We explored the constituents of TBE and TAE as prepared by major biotechnology suppliers, laboratories within our institution, and standard laboratory manuals (such as Molecular Cloning) (1, 9). Various protocols use either free acid EDTA (Invitrogen), disodium EDTA (Molecular Cloning)(1, 9), or tetrasodium EDTA (USB) (see Table 1). Although this might appear to be a trivial difference, media containing equimolar EDTA of different forms behaved quite differently. As expected from the above results (FIG. 1d), media containing EDTA (acid) had the least initial current and maintained a reduced current over time as compared to the two other forms of EDTA that contained additional sodium (FIG. 1e). We concluded that amounts of sodium capable of generating significant current are included in common media. Another protocol specified NaAc to be added to TAE along with disodium EDTA (see Table 1), perhaps a holdover from the use of sodium acetate in conductive buffers for RNA gels in the 1960's (7, 15). At that time, the NaAc was added with the intention to maintain the secondary structure of the RNA, most likely having no purpose when carried over to DNA electrophoresis (15). EDTA, introduced initially into the sample buffer to prevent RNA from remaining at the origin, is now superfluous, since most DNA samples are readily soluble and since commonly used enzymes today would not carry an undesirable enzymatic activity under electrophoretic conditions (15). The addition of free acid EDTA into the conductive media would be minimally conductive, for situations where EDTA may be specifically desired.

TABLE 1

Constituents and characteristics of conductive media for DNA electrophoresis.

| Media | Tris (mM) | Na+ (mM) | Li+ (mM) | Voltage range (V/cm)[9] |
|---|---|---|---|---|
| TAE[1] | 40 | 6 | 0 | 5-10 |
| TAE[2] | 40 | 10 | 0 | 5-10 |
| TBE[3] | 89 | 0 | 0 | 5-10 |
| TBE[4] | 89 | 4 | 0 | 5-10 |
| TBE[5] | 89 | 8 | 0 | 5-10 |
| SCA[6] | 0 | 12.5 | 0 | 5-10 |
| Na boric acid[7] | 0 | 10 | 0 | 5-50 |
| Li boric acid[7] | 0 | 0 | 10 | 5-50 |
| Li boric acid[8] | 0 | 0 | 1 | 5-150 |

Protocols from:
[1]Maniatis (contains 2 mM diNaEDTA),
[2]Hayward (2 mM diNaEDTA),
[3]Invitrogen (2 mM free acid EDTA),
[4]Maniatis (2 mM diNaEDTA),
[5]USB (2 mM tetraNaEDTA),
[6]novel media at 12.5 mM cation concentration.
[7]novel media at 10 mM cation concentration and.
[8]novel media at 1 mM cation concentration.
[9]V/cm = voltage applied to electrophoretic rig, per cm of gel length to produce optimal resolution of separated DNA fragments in 5 mm thick agarose horizontal gels.
Li, lithium; Na, sodium.

Figure 2:
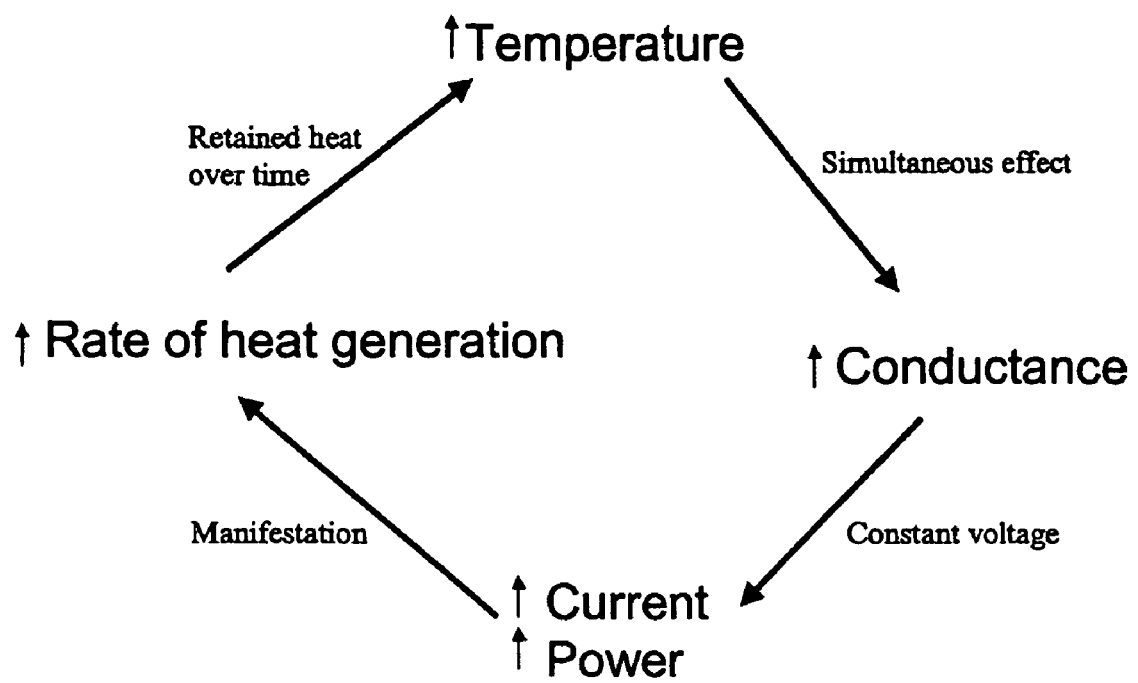
FIG. 2 shows a schematic representation of the "runaway" positive feedback loop created by an increase in temperature and conductance of the conductive media during electrophoresis.

These commonly used buffers thereby create a "runaway" positive feedback loop of current and temperature (FIG. 2). For most TBBs, this positive loop results in poor gel resolution at high voltage and a necessity for low voltage runs (5-10V/cm).

Example 3

Alternative Media

We thereby explored alternative, simplified conductive media that could mitigate this feedback loop. A reduced concentration of Tris-acetic acid (stripped of NaAc and EDTA) was sufficient for DNA electrophoresis (30 mM Tris; adjusted to pH 8 with glacial acetic acid to about 20 mM acetate) (Table 1), while lower concentrations of this solution provided poorer gel resolution (data not shown). This optimal Tris-acetic acid media (OTA) (Table 1) outperformed TAE and was comparable to TBE in the desirable properties investigated (FIG. 1a-c). OTA gels could be run faster than TAE gels (i.e. at high voltage, 25V/cm) as well as at standard electrophoretic conditions (10 V/cm) (data not shown). Interestingly, although chloride might not be the optimal anion for TBBs, a standard commercial TE solution at 3× provided adequate gel resolution (see Materials and Methods, data not shown).

Figure 3A:
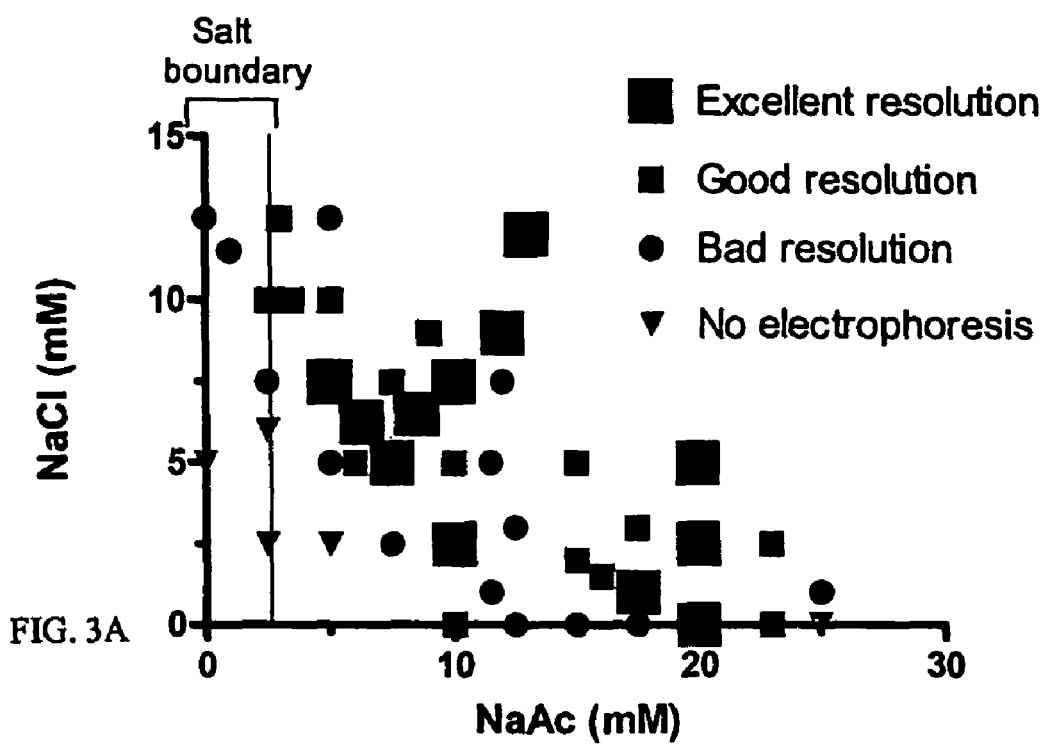
FIGS. 3A-3C show SCA (sodium chloride and acetate) islands.
Figure 3B:
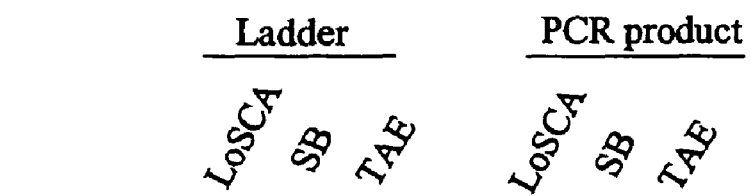
Figure 3C:
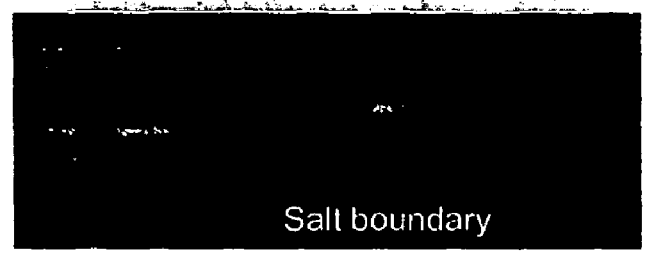

Conductive media using low molarity alternative cations were explored. Media based on sodium chloride and NaAc (SCA) were derived empirically (FIG. 3a-c). Combinations of particular concentrations (SCA islands) permitted high resolution of DNA fragments under standard electrophoretic conditions (FIG. 3b). Alternate anions could be substituted into SCA; sodium phosphate, sodium bicarbonate, and sodium salicylate could replace sodium acetate in SCA (data not shown). Similarly, other cations, provided by potassium chloride with potassium acetate or by ammonium acetate with ammonium chloride, could be adequately used at SCA concentrations (7.5 mM acetate and 5 mM chloride) (data not shown). FIGS. 4b-d show the empirical nature of discovering or "mapping" SCA. NaCl has a known ability to disrupt complexes of DNA with itself or buffer, a property that may contribute to the observation of optimal composite media (11). Analysis of three distinct SCA media concentrations (HiSCA, SCA, and LoSCA) showed all to have adequate gel resolution, with LoSCA conducting the lowest current and best resolution over a prolonged time (FIGS. 4b and c and data not shown). Therefore, LoSCA was chosen for further analysis of SCA gels. Although LOSCA media outperformed other SCA points, we found that midSCA (see table 1 and FIG. 3a) was less "finicky" as to tolerable ionic concentrations as compared to LOSCA, which resided in a narrow area within the SCA islands (FIG. 3a). Higher concentrations of sodium chloride produced a salt boundary which could presumably be avoided with reservoirs of larger volume (FIGS. 4a and c).

Figure 4A:
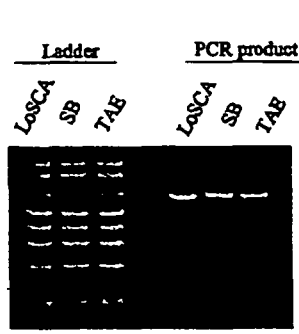
FIGS. 4A-4C show SB (sodium boric acid medium) performance in agarose DNA electrophoresis.
Figure 4B:
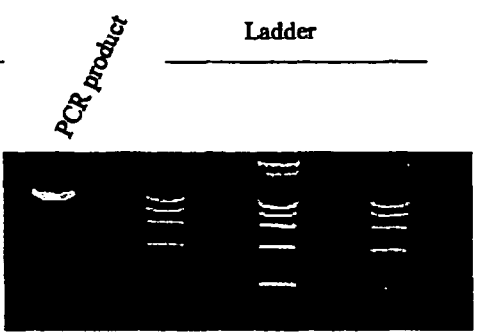
Figure 4C:
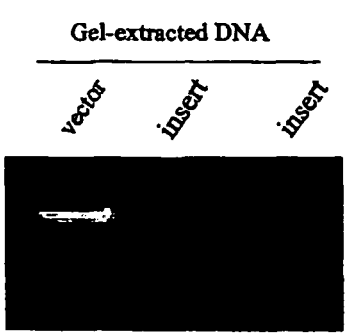

We then explored the borate requirements of our sodium-based series of low-conductant media Empirically, 10 mM sodium boric acid (10 mM sodium provided by 5 mM disodium borate decahydrate or by 10 mM sodium hydroxide, adjusted with boric acid to a pH of 8) was excellent at standard electrophoretic conditions (FIG. 4a, see table 1 for description of media). Sodium boric acid (SB) resolved best within a narrow range of 7.5 mM and 12.5 mM (data not shown). Potassium boric acid (potassium hydroxide titrated to pH=8 with boric acid) was similarly excellent as a conductive medium (data not shown).

SB medium was able to essentially abrogate the "runaway" feedback loop of increasing current and temperature (FIG. 1a-c). LOSCA performed better than TAE in analysis of the feedback loop (FIG. 1a-c), yet was unable to mitigate the feedback loop to the same extent as SB. SB had only slightly increased temperature and current over time and thus proved to be an outstanding conductive media for electrophoresis.

Extending our comparison of TBB and Tris-less media, it was of interest to directly compare Tris to sodium ions. Tris, spiked into SB, required nearly ten-fold higher concentration to cause a comparably increased current in a Tris-less system, as compared to the amount of NaCl or NaAc required in a TBB system. This result was consistent with the higher molar conductivity of sodium ions (FIGS. 1d,e) (16). Consequently, TBB media usually incorporate 40 to 80 mM Tris.

The new low-conductive media allowed achievement of ultra-fast electrophoretic separation using higher voltages. For example, agarose gels using SB at high voltage (30V/cm or 300 volts in a small gel rig, see table 1) resulted in a high-resolution separation within 13 minutes (FIG. 4b), similar to such a gel run at a standard voltage (10V/cm) for 1 hour and 30 minutes (FIG. 4a). Gel extraction of restriction-digested plasmid DNA was performed in SB gels for cloning experiments (FIG. 4c). A stock of 10×-50× can be stored without the occurrence of precipitation over time as occurs with tris boric acid. While SB is advantageous, a borate-free alternative is provided by SCA medium (see table 1) or by lithium acetate (table 1 and presented below).

The above study used agarose gels. SB was also successfully used in non-denaturing and denaturing (6%-20%) polyacrylamide gels. Denaturing gels with urea showed adequate electrophoretic resolution, optimally with the inclusion of 1×SB and ficoll-400 in the formamide loading solution (data not shown). Non-denaturing gels (6% and 20%) were able to resolve 100 base pairs and below (data not shown). SB, in the polyacrylamide system, reduced the current and implicitly the heat generation at high voltage compared to 1×TBE buffer. Polyacrylamide denaturing and non-denaturing gels also performed adequately with potassium boric acid (10 mM potassium ion) and SCA (data not shown).

Example 4

Electrolyte Exhaustion

Figure 5A:
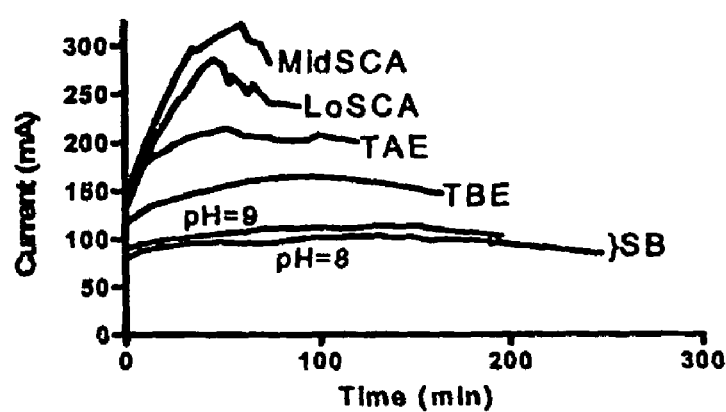
FIGS. 5A-5C show electrolyte exhaustion and pH changes over time.
Figure 5B:
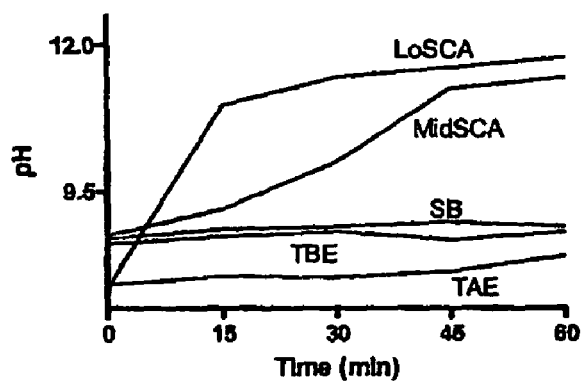
Figure 5C:
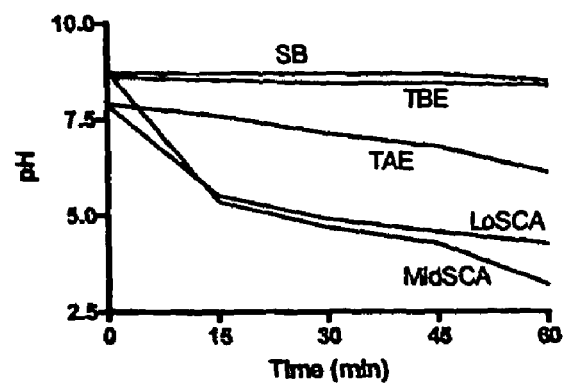

SB (pH=8) had a delayed electrolyte exhaustion at constant voltage as compared to other media tested (FIG. 5). Electrolyte exhaustion occurred at 3 hours for SB, but at less than one hour for TAE, as determined by observing the current at a constant voltage (FIG. 5). In this regard, SB outperformed every conductive media tested: SCA, LoSCA, TAE, and TBE. Indeed, TBE outperformed TAE, most likely due to the boric acid, which by buffering the hydroxide production provides a continuing cathodic source of borate for conducting current. Along similar lines of explanation, SB pH=9 exhausted more rapidly than SB at pH=8 (FIG. 5a). At the lower pH, boric acid represents a larger reserve to replenish ions at the cathode. One would expect that boric acid-containing media could be used for longer runs without recirculation. For prolonged runs involving a reuse of media, recirculation and replenishment of boric acid ($H_3BO_3$) and borate (borate acid ion, $H_2BO_3$—) from the anodic chamber to the cathodic is feasible, but acetate, once destroyed at the anode, cannot be recirculated. The substitution of sodium salicylate for NaAc in SCA solution illustrated this reaction class. The anodic chamber became bright yellow due to the oxidative decarboxylation of salicylate followed by oxidative meta-cleavage of the catechol intermediate to form 2-hydroxy muconic semialdehyde (data not shown) (17). pH changes in the anodic and cathodic chambers of TBBs and sodium-based media were indeed observed during electrophoresis (FIG. 5c). In contrast to all other media tested, TBE and SB were able to maintain a constant pH of nearly 8 in both electrode chambers (FIGS. 5b and c). Of note, acetate media should not be considered as buffered solutions, when used at a pH range desirable for DNA.

Example 5

Miscellaneous Properties

We also demonstrated several interesting and expected properties that we nonetheless know to relate to some common misconceptions among investigators that perform electrophoresis. First, an increased volume of buffer in the gel rig increased both the current and the temperature during electrophoresis at constant voltage (data not shown). Some investigators regrettably presume that the addition of extra buffer would act as a heat sink for the gel. Second, the voltage applied by the power source greatly exceeded that applied to the gel. In all buffered systems tested, the measured voltage "seen" by the gel (using voltmeter probes) was roughly half of the setting on the power supply when tested across the gel (data not shown). Further, the potential differences across the "upper" and "lower" halves of the gel were equivalent and stable over the course of a standard electrophoretic run. The electrophoretic force experienced by each segment of the gel thus was consistent with the concept of field strength, calculated by dividing volts by distance, although this would be modified by exhaustion of individual ionic species through migration (2, 9). Most of the remaining voltage drop and power consumption is assumed to be attributable to the electrolysis of water. The values of field strength given in this report conform to the convention in the literature to specify the voltage delivered, rather than that experienced by the gel.

Third, in searching for a better conductive media as judged by reduced current, temperature generation, and gel resolution, we found that TBE was a better medium than TAE (FIGS. 1A-C, 5). Fourth, 5 mm thick gels were adequate for horizontal electrophoresis, while thicker gels produced increased heating due to increased current (data not shown). Finally, DNA electrophoresis buffers are normally adjusted between pH 7.9-8.0 but since nucleic acids are highly acidic, it is known that DNA electrophoretic separation should withstand pH changes within a wide range (2). We found that most gels at various pH from 7.5 to 9.3 produced similar results (data not shown). We also found that low-concentration conductive media did not "exhaust" faster, a favorable finding that is attributable to a lower current which compensated for the reduction in the ionic reserves.

In summary, it is possible to mitigate the "runaway" positive feedback loop with new, simple conductive media, along with considerable savings in cost and time (Table 1).

We roughly estimate that the new conductive media could save the United States over 90 million dollars annually, allowing better temperature control, improved portability and convenience by reduced power and amperage requirements of the power supply, and a decreased need for heat dissipation in the electrophoretic device.

It is instructive, in light of the above studies, to revisit the history of the current buffers to examine how suboptimal buffers might have come to dominate DNA electrophoretic technology in preference to simpler and better media. It is our thesis that the explanation lies in the systematic development of these media which lacked a comprehensive analysis of the constituents. For example, borax and, later, varied borate solutions were found to allow the electrophoretic migration and thus separation of otherwise neutral carbohydrates, such as glucose and maltose (20). Comparative studies found that, to drive the formation of the borate-carbohydrate complexes, one required an optimal pH as well as higher concentrations of the borate solutions, such conditions allowing maximal migration rates in an electric field. The later specification of tris as a favored counter-ion provided additional buffering ability and would have mitigated the known and limiting problem of ohmic heating.

DNA, however, does not require full complexation with borate to provide optimal electrokinetic behavior, for DNA is naturally charged in all solutions in which it is chemically stable. Borate concentrations thus exceeded those needed for electrophoretic separation. Yet, there was now a Catch-22 for any efforts to simplify the medium. The dilution of borate in DNA electrophoretic separative media was limited by the poor resolution of low-conductance tris buffers, and the simple substitution of a more electromotile counter-ion was limited by ohmic heating of the high-concentration borate solutions. Similar barriers impeded the modification of tris-acetate buffers. The substitution of a metal ion as the predominant counter-ion required the simultaneous modification of ionic species and concentrations.

Example 6

Resolution of Small and Large DNA Fragments and of RNA

Materials and Methods. Gels were 1.0% agarose (Type I low EEO, Sigma, St. Louis, Mo.) unless otherwise indicated and contained 0.2 microgram/ml ethidium bromide (Fisher Scientific, Fair Long, N.J.). The power source displayed current flow (milliamps) at set voltages (250, 300, and 1000 volts (V)). $\Delta T$ (° C.) was calculated by subtracting the initial from the final temperature of the media in the anodic chamber. All DNA electrophoretic runs used a horizontal rig (MGU-500, CBS, Del Mar, Calif.) and had 650 ml total volume of medium in the reservoirs. Gels were 10 cm in length. 1 Kb-plus (Invitrogen, Carlsbad, Calif.) and 20 bp (GenSura, San Diego, Calif.) DNA ladders were loaded as indicated. For DNA, loading media was an Orange G (Sigma) based 10% glycerol (USB, Cleveland, Ohio) in solutions to match the cognate 1× conductive media in use.

Short oligomers of ssDNA were separated in 1 mM lithium boric acid medium. A 35 bp oligomer was mixed in parallel with 36, 38, and 45 bp oligomers (40 ng each), respectively, and heated to 70° C. for 5 min to denature potential dimers. Samples were loaded at 370° C. and separated for 25 min at 29 V/cm.

For RNA gel electrophoresis, an RNA ladder (#361, New England Biolabs, Beverly, Mass.) was used. For each run, 200 ng of ladder in 1.8 uL of loading medium (4.5% glycerol, 7.5% formaldehyde, 57% formamide, 40 ug/mL ethidium bromide) was denatured at 70° C. for 2 min, placed on ice for 2 min and loaded onto denaturing gels containing 1% agarose, 0.67% formaldehyde, and either 5 mM sodium boric acid or 5 mM lithium acetate in the gel and reservoirs. Gels were run at 400 V (40 V/cm) for 10 min in a CBS scientific MGU-200T horizontal mini gel system. Current was observed by methods similar to those described for DNA electrophoresis.

Results/Discussion. Sodium boric acid (10 mM sodium) permitted high-voltage rapid DNA electrophoresis (18). Empirically, in specialty applications it proved possible to further reduce the ionic concentrations and current of conductive media by another five- to ten-fold. Salt solutions of alkali metals (lithium boric acid, rubidium boric acid, potassium boric acid, cesium boric acid) and a simple, non-biologic buffer amine (ethanolamine with boric acid) were tested at various concentrations (19). At 1 mM cation concentration, DNA fragments were separated with minimal conductivity (FIG. 6A). Notably, these solutions separated small DNA fragments at a very high voltage (1000 V, 100 V/cm, FIG. 6). These low-concentration solutions did not generate significant heat in an electrophoretic system, unlike common electrophoretic media, and thus were run roughly 15-fold faster than is conventional practice (FIG. 6A, TAE and TBE run at 5-10 V/cm; new conductive media, up to 150V/cm, not shown). Further, these low-molarity media served well in separating small DNA fragments in agarose gels that normally would require polyacrylamide (FIG. 6A and 6C). Electrolyte exhaustion was measured by observing the current over the course of the electrophoretic runs; the current of the 1 mM solutions did not drop more than 15% during these runs (FIGS. 6A and 6B).

Lithium boric acid outperformed other low molarity media in its low conductivity and minimal heating (FIG. 6). One-mM lithium boric acid (3.0% agarose gel) was able to resolve 1-base pair differences between ssDNA oligomers in the absence of a chemical denaturant and without requiring high temperatures (FIG. 6C). Gel purification of an oligomer in 1 mM lithium boric acid yielded high recovery of the ssDNA fragment (Spin-X, Costar, Cambridge, Mass.)(not shown). Low molarity media readily permitted preparation of higher density agarose gels (3.0% agarose, FIG. 6C).

Although boric acid provides an exceptional anion for DNA electrophoresis (1, 18, 19), we found that alternative non-borate anions produced greater separation of high molecular weight (>2.0 Kb) DNA fragments (not shown). Lithium acetate (5 mM)(1×) produced low current and heat, thus allowing for fast separation of the longer DNA fragments in 1.0% agarose gels (FIG. 7A)(19). In comparison, TAE gels melted within 30 min at such high voltage (30 V/cm, not shown).

Low-molarity media were also successful in separating RNA in agarose gel electrophoresis (FIG. 7B). Sodium boric acid (5 mM, pH=6) (0.5×) and lithium acetate (5 mM) resolved RNA within 10 minutes (400 volts, 40V/cm, FIG. 2C)(18). These low-molarity media resolved RNA under lower heat and conductive conditions than the conventional MOPS medium (FIG. 7B)(19).

A positive runaway feedback loop exists in DNA electrophoresis between temperature and current when using tris-based solutions (TAE and TBE) (FIG. 6A) (9, 18, 12). New conductive media mitigate this feedback loop and allow for ultra-fast separation of small and large DNA and RNA fragments in an easy-to-use agarose system (FIGS. 6 and 7). Lithium had the lowest current of the alkali metal series, consistent with its larger shell of hydration. Conversely, and as expected, cesium and rubidium had the highest conductivity due to their smaller radii of hydration (FIG. 6). One-mM solutions performed well in electrophoresis irrespective of concern for buffering capacity, and thus it is best to label these solutions as conductive media rather than as 'buffers.'

For standard applications of slab gel DNA electrophoresis (100 bp to 5.0 Kb separations), we recommend 110 mM sodium boric acid be used. In special situations, such as high resolution separation of longer DNA fragments (>3.0 Kb) we recommend 5 mM lithium acetate (FIG. 7A). Where adequate attention can be devoted to reduction of salt in the sample analyzed, 10 mM lithium boric acid is recommended for small and mid-sized DNA fragments (<3.0 Kb). 5 mM sodium boric acid and 5 mM lithium acetate media can be used in place of MOPS for RNA separation (FIG. 7B). One-mM lithium boric acid agarose gels can be used in place of polyacrylamide for separation of small DNA and ssDNA fragments (FIG. 6). Other choices are not precluded, but these appeared optimal under the conditions tested.

Low-molarity media mitigates the positive feedback loop that exists with existing media and can be used to separate very small or large fragments of DNA in agarose gels, outperforming the commonly used media in the above-examined applications. These findings should improve the speed, cost-effectiveness, and practicality of many genetic-based investigations.

REFERENCES

1. Sambrook, J., Fritsch, E. F. & Maniatis, T. (1989) *Molecular cloning: a laboratory manual* (Cold Spring Harbor Laboratory, Cold Spring Harbor, N.Y.).
2. Aaij, C. & Borst, P. (1972) *Biochim Biophys Acta* 269, 192-200.
3. Hayward, G. S. & Smith, M. G. (1972) *J Mol Biol* 63, 383-95.
4. McDonell, M. W., Simon, M. N. & Studier, F. W. (1977) *J Mol Biol* 110, 119-46.
5. Thorne, H. V. (1966) *Virology* 29, 234-9.
6. Stellwagen, N. C., Bossi, A., Gelfi, C. & Righetti, P. G. (2000) *Anal Biochem* 287, 167-75.
7. McPhie, P., Hounsell, J. & Gratzer, W. B. (1966) *Biochemistry* 5, 988-93.
8. Maniatis, T., Fritsch, E. F. & Sambrook, J. (1982) *Molecular cloning: a laboratory manual* (Cold Spring Harbor Laboratory, Cold Spring Harbor, N.Y.).
9. Brody, J. R. and Kern, S. E. (2004) *Analytical Biochemistry* 333, 1-13
10. Stellwagen, N., Gelfi, C. & Righetti, P. G. (2002) *Electrophoresis* 23, 167-75.
11. Stellwagen, E. & Stellwagen, N. C. (2002) *Electrophoresis* 23, 1935-41.
12. Hjerten, S. (1973) *Ann N Y Acad Sci* 209, 5-7.
13. Hawcroft, D. M. (1997) *Electrophoresis* (IRL Press at Oxford University Press, Oxford N.Y.).
14. Allen, R. C. & Budowle, B. (1994) *Gel electrophoresis of proteins and nucleic acids: selected techniques* (W. de Gruyter, Berlin; New York).
15. Loening, U. E. (1967) *Biochem J* 102, 251-7.
16. Ng, B. & Barry, P. H. (1995) *J Neurosci Methods* 56, 37-41.
17. Dagley, S. (1960) *Nature* 188, 560-566.
18. Brody, J. R. and Kern, S. E. (2004) *Biotechniques* 36, 214-216.
19. Brody, J. R. and Kern, S. E. (2004) *Biotechniques* 37, 598-602.
20. Foster, A. B. (1957) *Adv Carbohydr Chem* 12, 81-115.

We claim:

1. A gel for separating polynucleotides according to length of the molecules comprising:
   a matrix substance and a conductive medium which comprises at least 0.5 mM anions in addition to any chloride anions which are optionally present, and one to 25 mM of total ions, inclusive,
   wherein the conductive medium may contain an organic amine biological buffer at a concentration of less than 10 mM;
   wherein said conductive medium comprises sodium as a cation and borate as an anion and
   wherein said conductive medium comprises at least 1 mM sodium borate.

2. The gel of claim 1, wherein the conductive medium does not contain an organic amine biological buffer.

3. The gel of claim 2, wherein the matrix substance is polyacrylamide.

4. The gel of claim 2, wherein the matrix substance is agarose.

5. The gel of claim 2, wherein the conductive medium comprises less than 20 mM of total ions.

6. The gel of claim 2, wherein the conductive medium comprises at least 10 mM anions.

7. The gel of claim 2, wherein the conductive medium comprises at least 0.5 mM sodium ion.

8. The gel of claim 2, wherein the conductive medium has a pH of 5.5 to 10.

9. A solution for making a gel for separating polynucleotides according to length of the molecules comprising:
   a conductive medium which comprises at least 0.5 mM anions in addition to any chloride anions which are optionally present, and one to 25 mM of total ions, inclusive, and
   a polymerizing agent for polymerizing a gel matrix substance;
   wherein the conductive medium may contain an organic amine biological buffer at a concentration of less than 10 mM;
   wherein said conductive medium comprises sodium as a cation and borate as an anion; and
   wherein said conductive medium comprises at least 1 mM of sodium borate.

10. The solution for making a gel of claim 9 wherein the conductive medium does not contain an organic amine biological buffer.

11. The solution of claim 10, wherein the conductive medium comprises less than 20 mM of total ions.

12. The solution of claim 10, wherein the conductive medium comprises at least 5 mM anions.

13. The solution of claim 10, wherein the conductive medium comprises at least 0.5 mM sodium ion.

14. The solution of claim 10, wherein the conductive medium has a pH of 5.5 to 10.

15. An electrophoretic apparatus for separating polynucleotide molecules comprising:

a gel, two or more reservoirs contiguous with the gel, and an anode and a cathode in contact with the reservoirs, wherein the reservoirs and the gel comprise a conductive medium which comprises at least 0.5 mM anions in addition to any chloride anions which are optionally present, and one to 25 mM of total ions, inclusive, wherein the conductive medium may contain an organic amine biological buffer at a concentration of less than 10 mM;

wherein said conductive medium comprises sodium as a cation and borate as an anion; and wherein said conductive medium comprises at least 1 mM sodium borate.

16. The electrophoretic apparatus claim 15 wherein the conductive medium does not contain an organic amine biological buffer.

17. A method of forming a gel for separating polynucleotides comprising:

mixing a gel matrix substance and a conductive medium which comprises at least 0.5 mM anions in addition to any chloride anions which are optionally present, and one to 25 mM of total ions, inclusive, wherein the conductive medium may contain an organic amine biological buffer at a concentration of less than 10 mM, to form a pre-gel mixture; and incubating the pre-gel mixture under conditions in which a gel forms;

wherein said conductive medium comprises sodium as a cation and borate as an anion; and wherein said conductive medium comprises at least 1 mM of sodium borate.

18. The method of claim 17, wherein the conductive medium comprises less than 20 mM of total ions.

19. The method of claim 17 wherein the conductive medium does not contain an organic amine biological buffer.

* * * * *